US010188160B1

(12) United States Patent
McCain

(10) Patent No.: US 10,188,160 B1
(45) Date of Patent: Jan. 29, 2019

(54) GARMENTS HAVING COMPARTMENTS THAT SUPPORT POST-OPERATIVE DRAIN DEVICES

(71) Applicant: Aisha McCain, Pittsburg, CA (US)

(72) Inventor: Aisha McCain, Pittsburg, CA (US)

( * ) Notice: Subject to any disclaimer, the term of this patent is extended or adjusted under 35 U.S.C. 154(b) by 0 days.

(21) Appl. No.: 15/726,307

(22) Filed: Oct. 5, 2017

(51) Int. Cl.
*A41D 13/12* (2006.01)
*A41D 27/20* (2006.01)
*A41D 13/00* (2006.01)

(52) U.S. Cl.
CPC ..... *A41D 13/1245* (2013.01); *A41D 13/0012* (2013.01); *A41D 27/20* (2013.01); *A41D 2400/32* (2013.01); *A61M 2209/088* (2013.01)

(58) Field of Classification Search
CPC ............ A41D 13/1236; A41D 13/1245; A41D 13/1281; A41D 1/02; A41D 1/04; A41D 27/20; A41D 13/0012; A41D 13/1254; A41D 1/002; A41D 27/204; A41D 27/208; A41D 2400/32; A41D 1/18; A41D 1/22; A41D 10/00; A41D 13/1263; A61N 27/00; A61N 2209/088
USPC ................................. 2/114, 94; D2/720, 839
See application file for complete search history.

(56) References Cited

U.S. PATENT DOCUMENTS

| | | | | |
|---|---|---|---|---|
| 1,444,750 A | * | 2/1923 | Moore ................ | A41D 13/0012 2/94 |
| 1,520,962 A | * | 12/1924 | North ................ | A41D 13/0012 2/102 |
| 3,055,133 A | * | 9/1962 | Anderson ................ | A41D 1/04 2/102 |
| 5,142,702 A | * | 9/1992 | Piloian ............... | A41D 13/1245 2/102 |
| 6,574,800 B1 | * | 6/2003 | Leger ................ | A41D 13/1245 2/114 |
| 7,396,272 B1 | * | 7/2008 | Newlen .............. | A41D 13/1245 2/114 |
| 7,823,221 B2 | * | 11/2010 | Green ................... | A61F 5/4408 2/114 |
| D764,145 S | * | 8/2016 | Mathews ....................... | D2/828 |
| 2004/0226073 A1 | * | 11/2004 | McCullar ........... | A41D 13/1245 2/114 |
| 2006/0156450 A1 | * | 7/2006 | McGrath ................ | A41D 10/00 2/114 |

(Continued)

*Primary Examiner* — Amy Vanatta
(74) *Attorney, Agent, or Firm* — Imperium Patent Works; Amir V. Adibi; Andrew C. Palmer

(57) ABSTRACT

A garment with post-operative drain compartments along an interior of the garment is manufactured and provided to a user after a surgical procedure. The garment has a first plurality of post-operative drain compartments on a first side of the garment and a second plurality of post-operative drain compartments on a second side of the garment. Each of the post-operative drain compartments supports a reservoir of a post-operative drain. The user, typically after a surgical procedure involving post-operative drains as part of recovery, wears the garment and inserts the reservoir of a post-operative drain into one of the post-operative drain compartments. The garment supports at least six post-operative drain compartments. At least one of the post-operative drain compartments is disposed above at least two others of the post-operative drain compartments. In one example, each of the openings post-operative drain compartments remains open and does not include any fastening mechanism.

17 Claims, 8 Drawing Sheets

FRONT PERSPECTIVE VIEW OF GARMENT HAVING POST-OPERATIVE
DRAIN COMPARTMENTS WHEN WORN BY USER

(56) References Cited

U.S. PATENT DOCUMENTS

| | | | | |
|---|---|---|---|---|
| 2006/0253954 A1* | 11/2006 | Music | A41D 13/0051 | 2/115 |
| 2007/0113316 A1* | 5/2007 | King | A41D 13/1245 | 2/102 |
| 2007/0271672 A1* | 11/2007 | Lentini | A41D 13/1245 | 2/69 |
| 2008/0000006 A1* | 1/2008 | Ochoa | A41D 13/1236 | 2/114 |
| 2008/0184455 A1* | 8/2008 | Blume | A41D 13/1245 | 2/114 |
| 2008/0312615 A1* | 12/2008 | Hunter | A41D 13/0012 | 604/345 |
| 2010/0205720 A1* | 8/2010 | Ortega Astor | A41D 13/1281 | 2/247 |
| 2011/0041231 A1* | 2/2011 | Behrens | A41D 13/1245 | 2/69 |
| 2011/0302703 A1* | 12/2011 | Silverberg | A41D 13/0058 | 2/457 |
| 2012/0030851 A1* | 2/2012 | Kinder | A41D 13/1209 | 2/69 |
| 2012/0090072 A1* | 4/2012 | Oprandi | A41D 13/1245 | 2/114 |
| 2012/0291179 A1* | 11/2012 | Shea | A41D 27/20 | 2/102 |
| 2015/0216242 A1* | 8/2015 | Evans | A41D 13/1245 | 2/114 |
| 2015/0296896 A1* | 10/2015 | Laguna | A41D 13/1245 | 450/58 |
| 2015/0366276 A1* | 12/2015 | Kuzmanovski | A41D 13/1245 | 2/251 |
| 2016/0219951 A1* | 8/2016 | Schickel | A41D 13/1236 | |
| 2016/0331049 A1* | 11/2016 | James | A41D 13/1245 | |

* cited by examiner

FRONT PERSPECTIVE VIEW OF GARMENT WITH POST OPERATIVE DRAIN COMPARTMENTS

OPENING OF GARMENT HAVING POST-OPERATIVE
DRAIN COMPARTMENTS

POST-OPERATIVE DRAIN COMPARTMENT PINCHED OPEN
TO RECEIVE A POST-OPERATIVE DRAIN RESERVOIR

FRONT PERSPECTIVE VIEW OF OPENING OF GARMENT HAVING POST-OPERATIVE DRAIN COMPARTMENTS WHEN WORN BY USER

FRONT PERSPECTIVE VIEW OF GARMENT HAVING POST-OPERATIVE
DRAIN COMPARTMENTS WHEN WORN BY USER

GARMENTS HAVING COMPARTMENTS THAT SUPPORT POST-OPERATIVE DRAIN DEVICES

TECHNICAL FIELD

The described embodiments relate to garments, and more particularly garments that support post-operative procedures and treatment.

BACKGROUND INFORMATION

Surgical tubes and drains are often used in treating patients as part of post-operative care. Improper treatment of post-surgical areas may result in the accumulation of air or fluid, which could lead to infection of the wounded area. To prevent the undesirable accumulation of fluid, post-operative drains are typically used to remove these fluids from the surgical area. Proper use of post-operative drain usually reduces the risk of infection and tends to minimize tissue trauma. Multiple variables have an impact on the effectiveness of these drains including: the consistency of the draining fluid, the tube diameter and length, and the amount of negative pressure from the drain. Post-operative drains can be used in various types of surgeries, including abdominal, breast, and orthopedic procedures.

One common type of post-operative drain is an active drain. Active drains use a closed drainage system with low-pressure suction devices that continuously remove fluids against gravity. The active drain is attached to a collapsible reservoir that exerts negative pressure to pull accumulated fluids from the wound bed. The collection reservoir expands as it collects drainage. One example of an active post-operative drain is shown in FIG. 1 (Prior Art). A reservoir 2 is attached to a drain 3. In this example, the reservoir 2 has a bulb shape with a capacity of approximately 100.0 cubic centimeters and the drain 3 has dimensions of approximately 7.0 mm in radius and 20.0 cm in length. In another example, the shape and capacity of the reservoir 2 and drain 3 dimensions may vary based on the need. One commercially available version of the post-operative drain as shown in FIG. 1 is a Jackson-Pratt Drain (also referred to as a "JP Drain"). The drain 3 may also be referred to as a "tube" and the reservoir 2 may also be referred to as a "bulb".

One known technique is to provide one or two compartments along a garment that attaches to or is worn by a patient. The compartments may be on the outside or inside of the garment. The patient wears or attaches the garment and then inserts the post-operative drain inside the compartment. However, numerous shortcomings exist with these conventional garments. For example, many of these garments do not provide sufficient support, versatility, or ease of use that is desirable for patients that have undergone challenging medical procedures. A solution that overcomes these shortcomings is desired.

SUMMARY

A garment with post-operative drain compartments along an interior of the garment is manufactured and provided to a user. The garment is worn and used by the user after the user has undergone a surgical procedure that involves a post-operative drain. Patients that undergo certain surgeries (e.g.—Plastic, Breast, Chest, Pancreatic, Biliary, Thyroid, and Neuro) will generally result in a buildup fluid in the surgical area. After the surgery, one or more post-operative drains are attached to the person's body to help prevent the accumulation of fluid. The post-operative drain compartments of the garment support and retain the one or more post-operative drains.

Each of the post-operative drain compartments supports a reservoir of a post-operative drain. The user wears the garment and inserts the reservoir of a post-operative drain into one of the post-operative drain compartments. A tube is inserted into the operated tissue and extends to a reservoir. The reservoir is also referred to as a bulb. The garment provides a mechanism for retaining the reservoir close to the body in an inconspicuous and convenient fashion. Users need not suffer as much embarrassment of being in public, as the reservoirs are concealed from the view of others. This is one significant improvement over the prior art. Conventional techniques are undesirably limited in the number and location of accessible pockets.

The garment has a plurality of post-operative drain compartments disposed along an inner surface of a side of the garment. At least one of the plurality of post-operative drain compartments is disposed above at least another one of the plurality of post-operative drain compartments. In one example, a first post-operative drain is at least 3.0 inches above a second post-operative drain compartment. In another example, a first post-operative drain is at least 5.0 inches above a second post-operative drain compartment.

By positioning one post-operative drain compartment above another, the garment provides significant ease and versatility to the user. This is because medical procedures may involve more than one drain situated along different parts of the individual's body. For example, a first tissue opening may be positioned above a second tissue opening after a medical procedure. For user comfort, the first tissue opening is connected to a first post-operative drain that is inserted into and retained within the upper positioned post-operative drain compartment. The second tissue opening is connected to a second post-operative drain that is inserted into and retained within the lower positioned post-operative drain compartment. Thus, the novel garment provides compartments that tend to be closer to each respective tissue opening than are provided in conventionally available garments.

In one embodiment, a garment has a first plurality of post-operative drain compartments disposed on a first side, and a second plurality of post-operative drain compartments on a second side of the garment. There are at least four compartments on the first side and four compartments on the second side that mirror the compartments on the first side. At least one compartment is disposed above two or more of the other compartments on a side. The numerous locations of compartments on various levels provide the user with flexibility in selecting his or her desired reservoir placement. This gives the user the ability to use multiple compartments simultaneously. For configurations supporting multiple reservoirs, the mirrored configuration allows for appropriate weight distribution between the left and right sides of the garment.

The garment has an attachment mechanism (e.g. Velcro, buttons, zipper, or another fastening instrument) that allows the user to open and securely close then garment when needed. The attachment mechanism does not impede the drains, but rather allows the user easy access to the post-operative drain compartments when garment is opened. When the garment is closed, the post-operative drain compartments remain secure and concealed from the public eye.

One novel aspect of the garment is the orientation of the post-operative drain compartments. At least one of the post-operative drain compartments is disposed above at least two others of the post-operative drain compartments. The garment supports at least six post-operative drain compartments. The drain compartments are versatile in that they allow for many options of where to put reservoir in the garment. There are several different configurations that can fit each user's needs. The compartments are organized in a way to facilitate proper drain circulation.

In one example, each of the openings post-operative drain compartments remains open and does not include any fastening mechanism. In this configuration, there is no zipper, Velcro, buttons, or any other fastening instrument to secure the opening. In another example, each of the openings of the post-operative drain compartments include a fastening mechanism (e.g.—zipper, Velcro, buttons, or other fastening instrument). In other embodiments, the garment may be other types of clothing including, a t-shirt, a long sleeve shirt, a pajama, a vest, a zip, a coat, and a jacket.

Further details and embodiments and methods are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
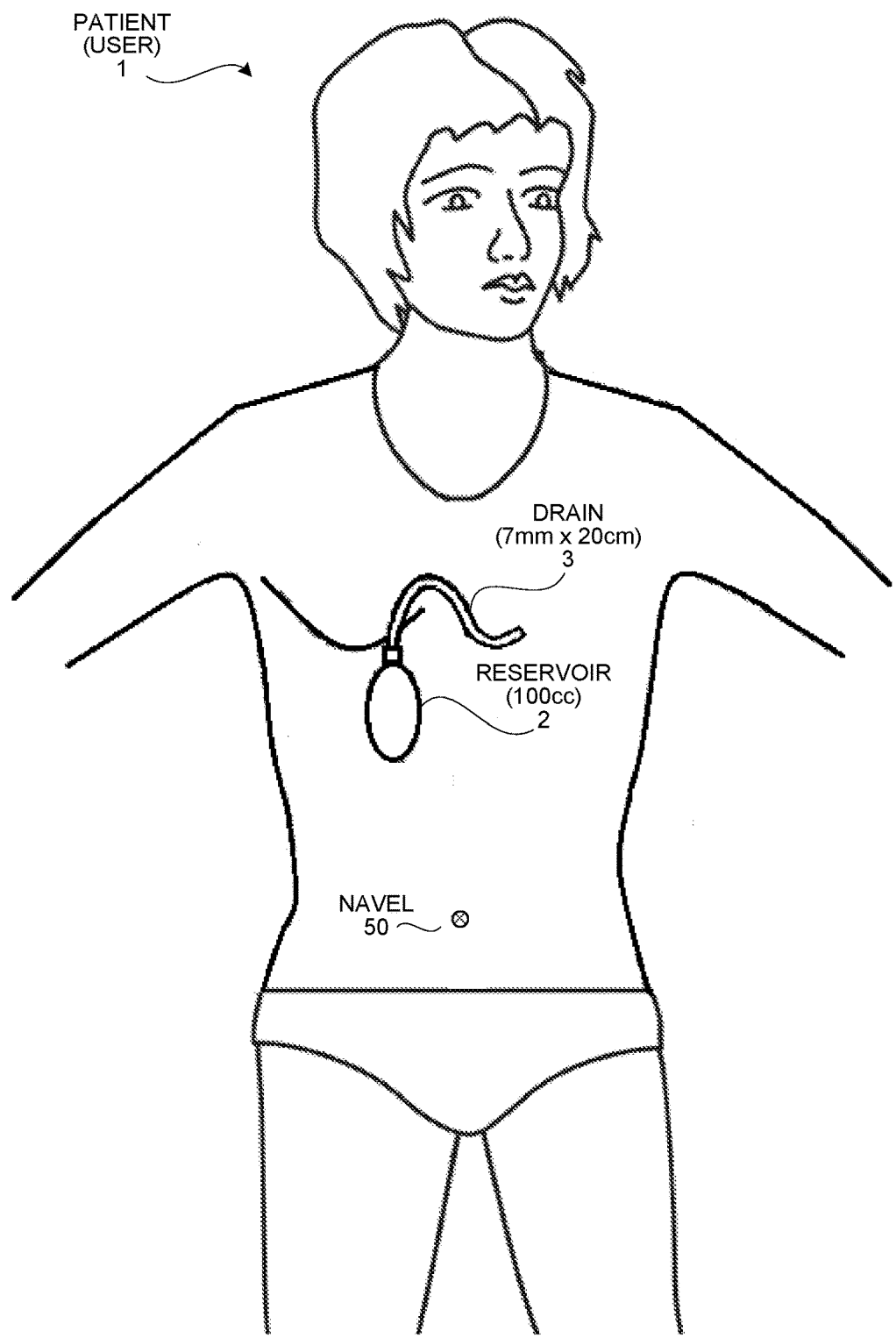
FIG. 1 (Prior Art) is a perspective diagram of a patient 1 using a post-operative drain 3 after a surgical procedure.
Figure 2:
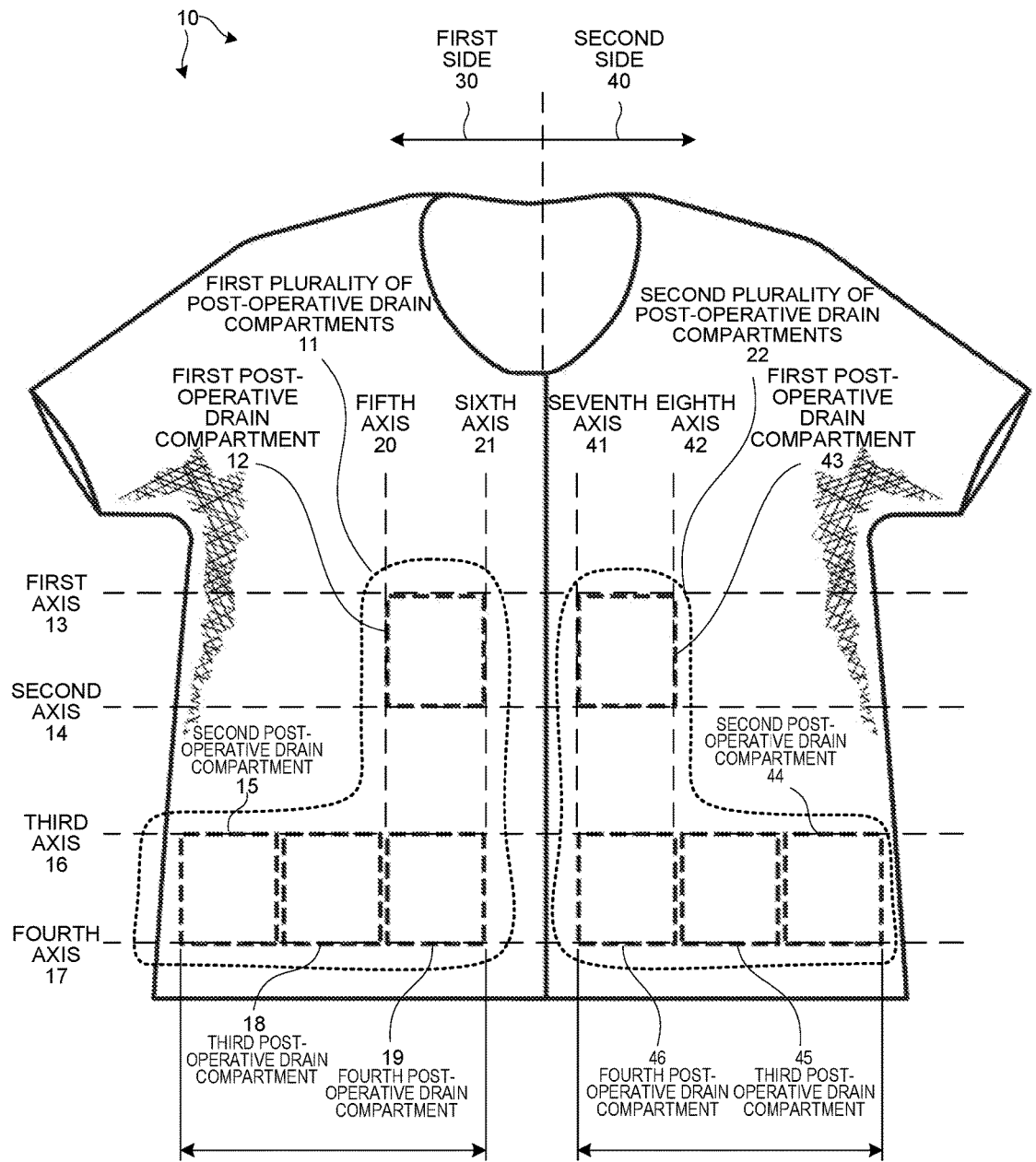
FIG. 2 is a diagram of a front perspective view of a garment 10 with post-operative drain compartments.

FIG. 2 is a diagram of a garment 10 having post-operative drain compartments. The garment 10 comprises a first side 30 and a second side 40. The first side 30 comprises a first plurality of post-operative drain compartments 11 and a second plurality of post-operative drain compartments 22. The first plurality of post-operative drain compartments 11 has a first post-operative drain compartment 12, a second post-operative drain compartment 15, a third post-operative drain compartment 18, and a fourth post-operative drain compartment 19. The second plurality of post-operative drain compartments 22 has a first post-operative drain compartment 43, a second post-operative drain compartment 44, a third post-operative drain compartment 45, and a fourth post-operative drain compartment 46.

In accordance with one novel aspect, the post-operative drain compartments are disposed along numerous axes described below. A first axis 13 is parallel to and above a second axis 14. The second axis 14 is parallel to and above a third axis 16. The third axis 16 is parallel to and above a fourth axis 17. On the first side 30, a fifth axis 20 is parallel to a sixth axis 21. On the second side 40, a seventh axis 41 is parallel to an eighth axis 42. The first, second, third, and fourth axes (13, 14, 16, 17) are perpendicular to the fifth, sixth, seventh, and eight axes (20, 21, 41, 42).

On the first side 30, the first post-operative drain compartment 12 is disposed horizontally between the first axis 13 and the second axis 14, and vertically between the fifth axis 20 and the sixth axis 21. The first post-operative drain compartment 12 is parallel to the fourth post-operative drain compartment 19. On the first side 30, the second, third, and fourth post-operative drain compartments (15, 18, 19) are disposed horizontally between the third axis 16 and the fourth axis 17. The fourth post-operative drain compartment 19 is disposed vertically between the fifth axis 20 and the sixth axis 21.

On the second side 40, the first post-operative drain compartment 43 is disposed horizontally between the first axis 13 and the second axis 14 and vertically between the seventh axis 41 and the eighth axis 42. The fourth post-operative drain compartment 46 is parallel to the first post-operative drain compartment 43. On the second side 40, the second, third, and fourth post-operative drain compartments (44, 45, 46) are disposed horizontally between the third axis 16 and the fourth axis 17. The fourth post-operative drain compartment 46 is disposed vertically between the seventh axis 41 and the eighth axis 42. By orienting the post-operative drain compartments in this way, the user of the garment is given significant versatility in securing post-operative drains.

Figure 3:
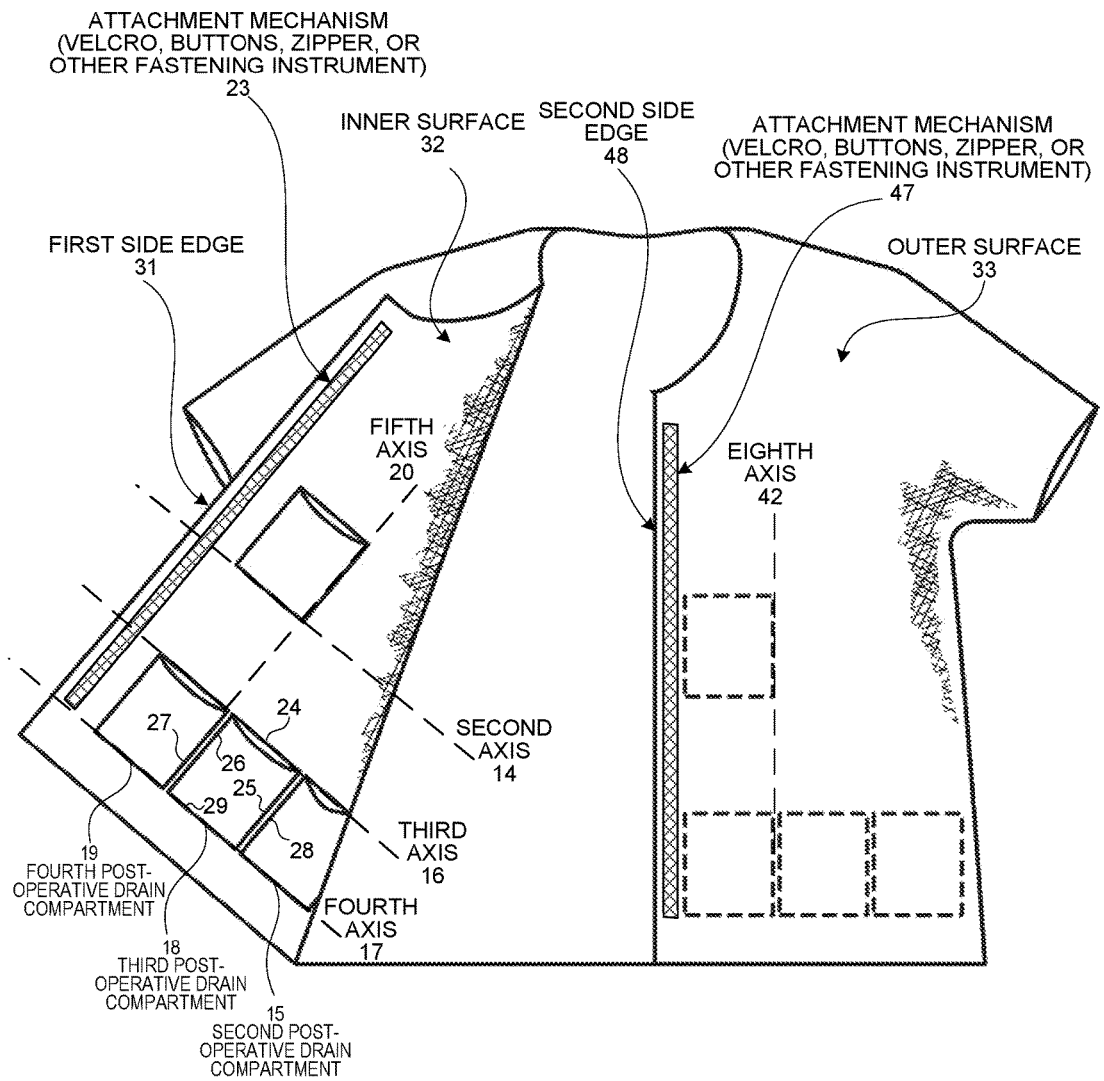
FIG. 3 is a diagram showing an inner surface 32 of the garment 10 having the post-operative drain compartments.

FIG. 3 is a diagram of an opening of a garment 10 having post-operative drain compartments. In this example, the third post-operative drain compartment 18 has four edges. A first edge 24 is disposed along the third axis 16. A second edge 25 is disposed along a fourth edge of the second post-operative drain compartment 28. A third edge 29 is disposed along the fourth axis 17. The fourth edge 26 is disposed along a second edge of the fourth post-operative drain compartment 27. In one example, the garment 10 is manufactured using natural fibers. In another example, the garment 10 is manufactured using synthetic fibers. In yet another example, the garment 10 is manufactured using a combination of natural fibers and synthetic fibers. In one example, the garment 10 comprises a material selected from the group consisting of: cotton, flax, wool, ramie, silk, denim, leather, down, fur, nylon, and polyester.

On an inner surface 32 of the first side 30, an attachment mechanism 23, for example, Velcro, buttons, zipper, or other fastening instrument, is along a first side edge 31 and parallel to the fifth axis 20. On the outer surface 33 of the second side 40, another attachment mechanism 47 that complements the attachment mechanism 23, for example, Velcro, buttons, zipper, or other fastening instrument, is along a second side edge 48 and parallel to the eighth axis 42.

Figure 4:
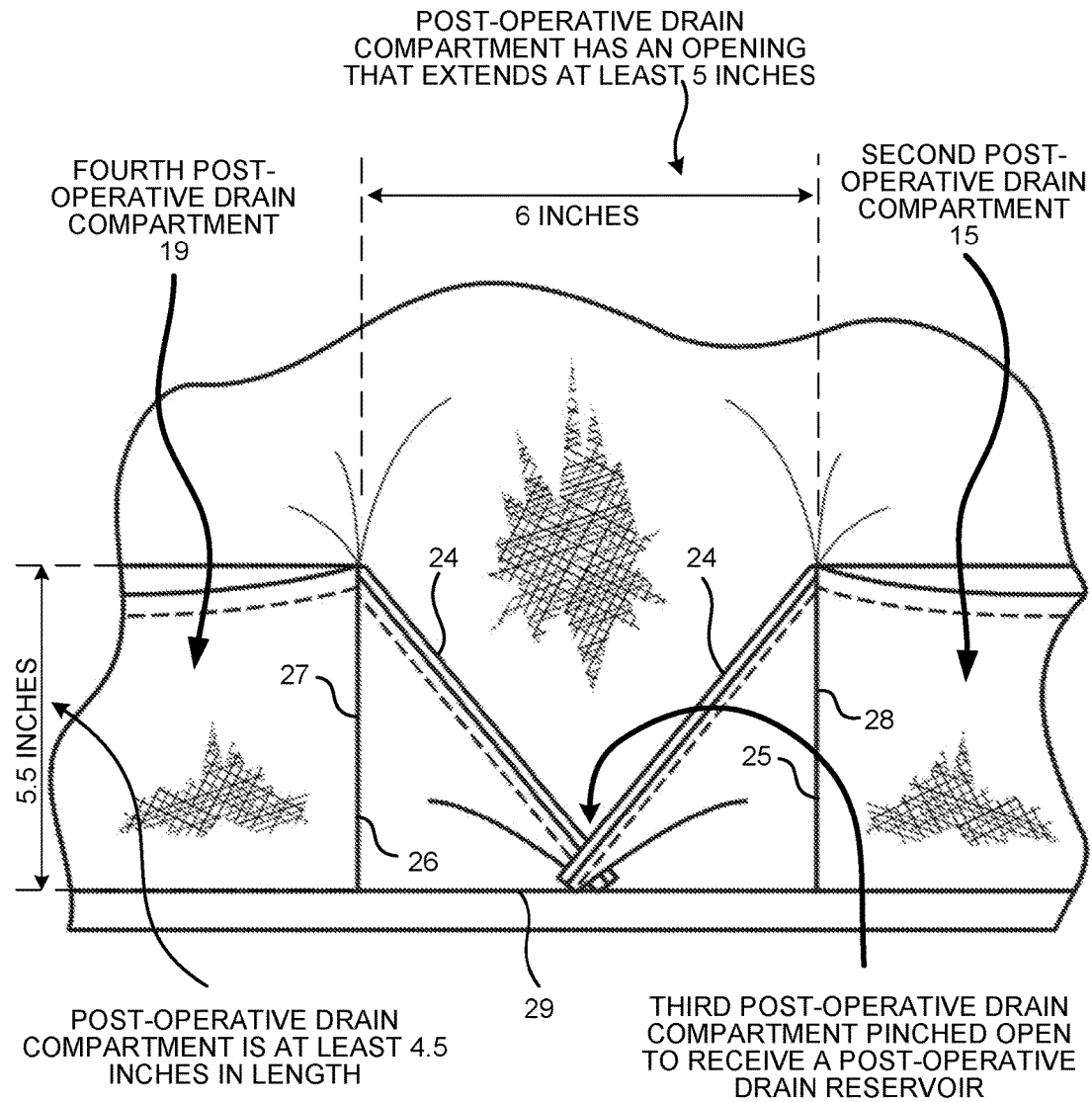
FIG. 4 is a diagram showing how one of the post-operative drain compartments is pinched open to receive a post-operative drain reservoir.

FIG. 4 is a diagram of a post-operative drain compartment pinched open to receive a post-operative drain. The first edge (or upper extent) of each of the plurality of the post-operative drain compartments has an opening that extends at least 5 inches. The second and fourth edges (or the side edges) of each of the plurality of the post-operative drain compartments extend at least 4.5 inches. These dimensions provide optimal retaining volume for reservoirs of typical post-operative drains. In this example, the first edge extends approximately 6.0 inches and the side edges extend approximately 5.5 inches.

In this example, each of the bottom and side edges of the post-operative drain compartment is stitched into the inner surface 32 of the garment 10. In another example, the post-operative drain compartments are glued onto the inner surface 32 of the garment 10. In another example, the post-operative drain compartments are attached to the inner surface 32 of the garment 10 using another attachment mechanism such as a safety pin, magnet, buttons, zippers, Velcro, or a combination of the above.

In accordance with another novel aspect, the upper edge of each post-operative drain compartment remains open thereby providing easy and quick storage of the post-operative drains. In the example of FIG. 4, the first edge of the third post-operative drain compartment 24 is shown pinched open to receive a post-operative drain. In one example, none of the post-operative drains has a closure mechanism or fastening mechanism that securely shuts the opening provided by the first edge (or upper edge). In the example of FIG. 4, the post-operative drains do not have any zipper, button, Velcro, or similar fastening mechanism and always remain open to provide ease of access. In another example, the post-operative drains have a closure mechanism or fastening mechanism that securely shuts the opening provided by the first edge (or upper edge), such as a zipper, button, Velcro, or similar fastening mechanism.

Figure 5:
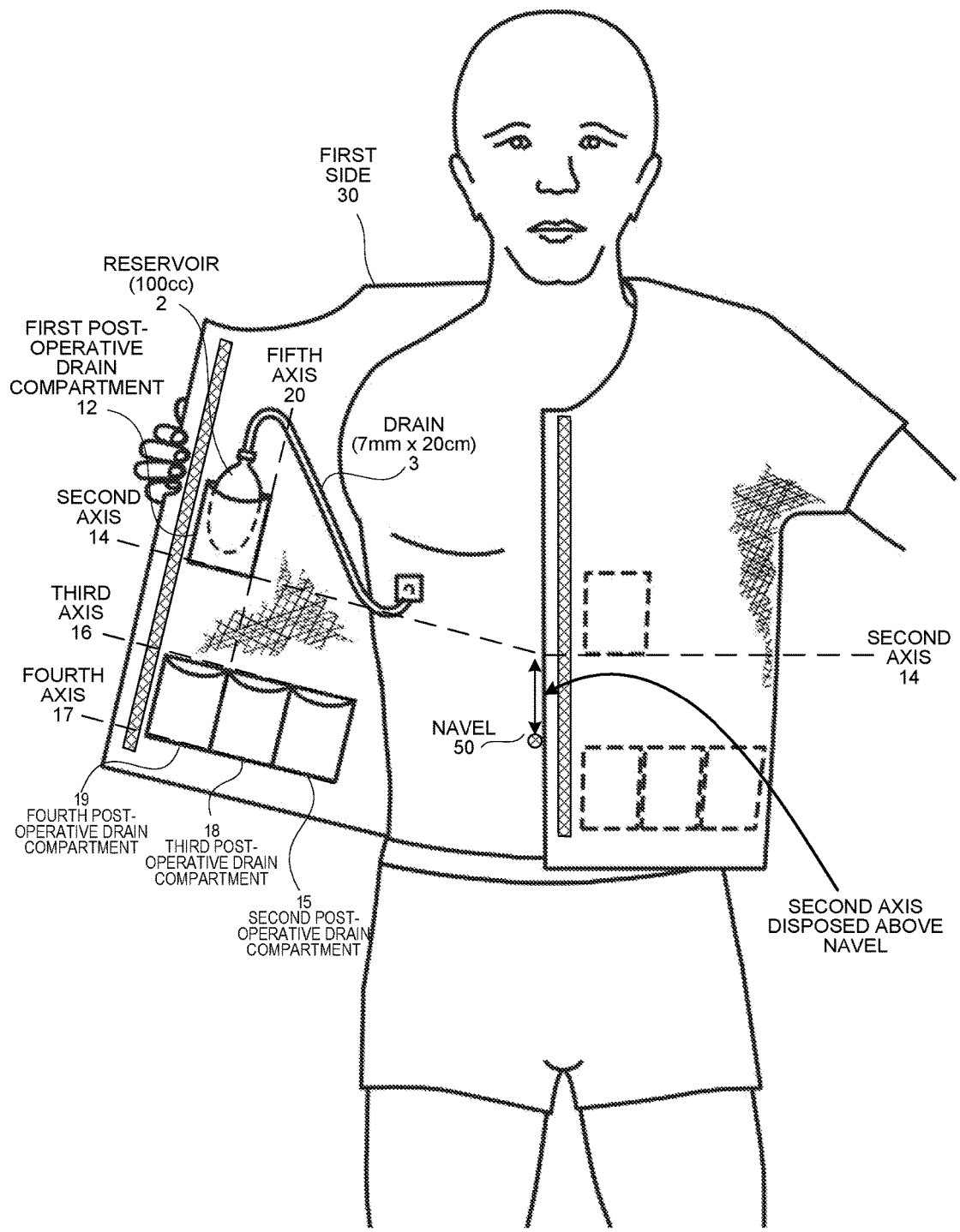
FIG. 5 is a diagram of a front perspective view of opening of a garment having post-operative drain compartments when worn by user.

FIG. 5 is a diagram of the front perspective view of the garment having post-operative drain compartments 10 when worn and opened. The second axis 14 is disposed above the navel 50. At least one post-operative drain compartment is disposed above the navel 50 when worn by the user and the at least one post-operative drain compartment is also disposed above another post-operative drain compartment that is disposed below the navel 50. In this example, the first post-operative drain compartment 12 is in use. In another example, other post-operative drain compartments may be used to support post-operative drains.

Figure 6:
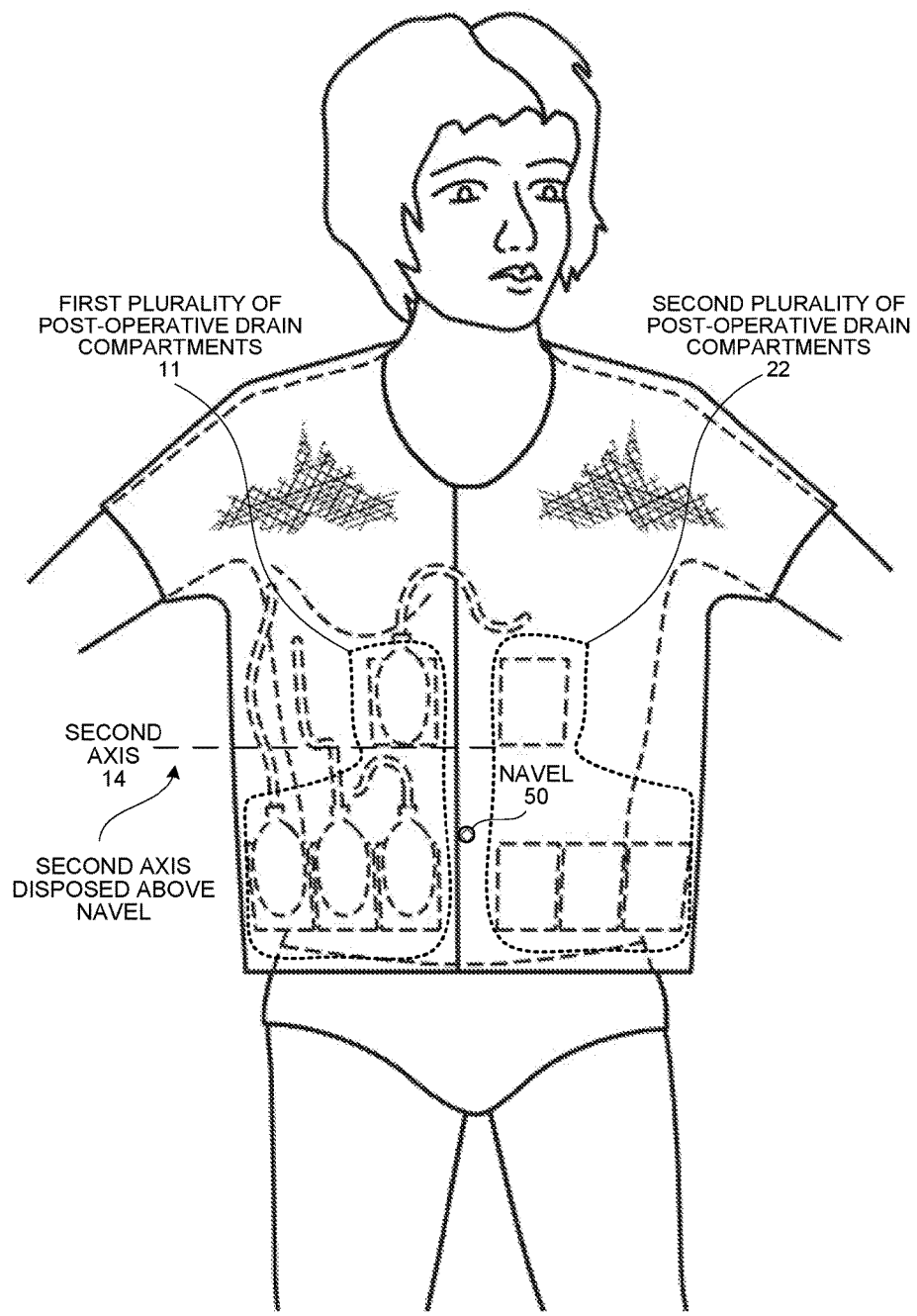
FIG. 6 is a diagram of a front perspective view of a garment having post-operative drain compartments when worn by user.

FIG. 6 is a diagram of the front perspective view of the garment having post-operative drain compartments 10 when worn and closed. The second axis 14 is disposed above the navel 50. In this example, each post-operative drain compartment in the first plurality 11 is in use. In another example, the second plurality of post-operative drain compartments 22 may be in use.

Figure 7:
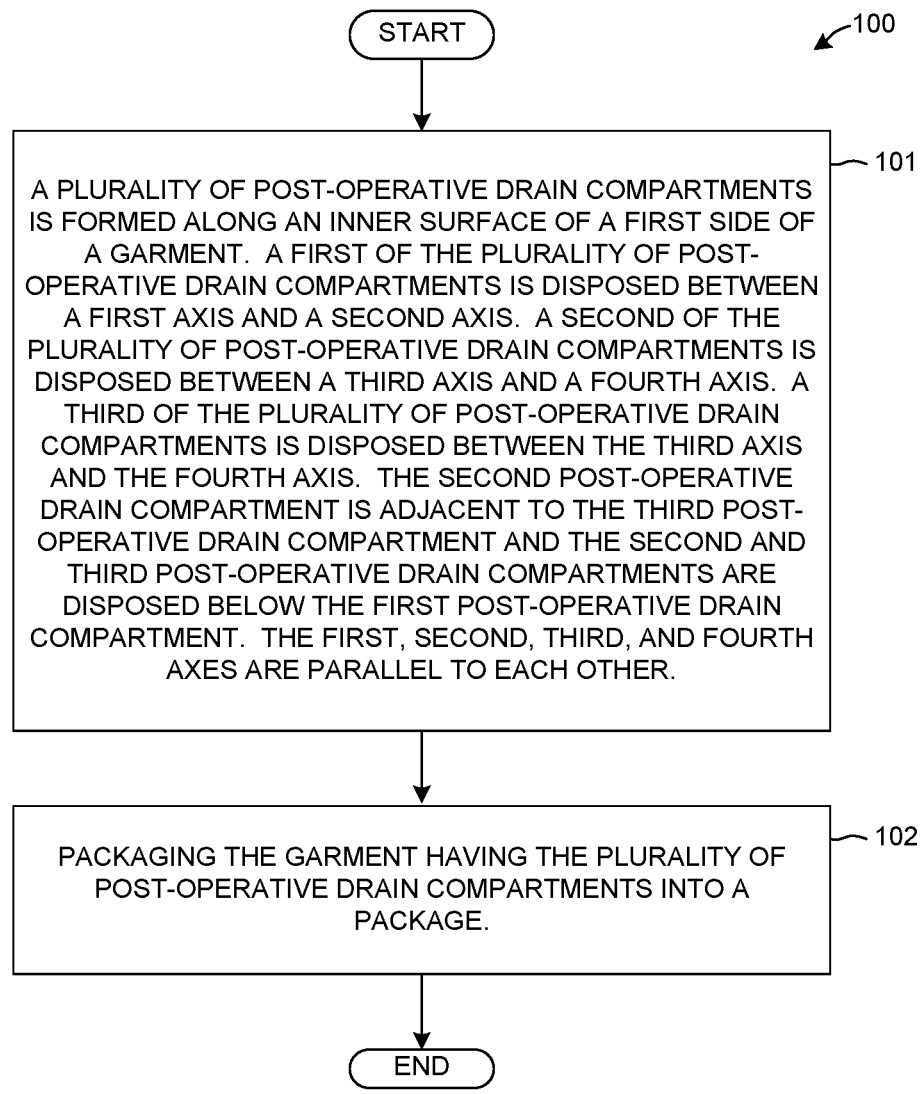
FIG. 7 is a flowchart of a method 100 in accordance with one novel aspect.

FIG. 7 is a flowchart of a method 100 in accordance with one novel aspect. In a first step (step 101), a plurality of post-operative drain compartments is formed along an inner surface 32 of a first side of a garment. A first of the plurality of post-operative drain compartments is disposed between a first axis and a second axis. A second of the plurality of post-operative drain compartments is disposed between a third axis and a fourth axis. A third of the plurality of post-operative drain compartments is disposed between the third axis and the fourth axis. The second post-operative drain compartment is adjacent to the third post-operative drain compartment and the second and third post-operative drain compartments are disposed below the first post-operative drain compartment. The first, second, third, and fourth axes are parallel to each other. For example, in FIG. 2, the garment 10 has a first plurality of post-operative drain compartments 11 formed along the inner surface 32 of the first side 30. There are a first, second, third and fourth post-operative drain compartments (12, 15, 18, 19) on the first side 30. In the example of FIG. 5, a reservoir (100 cc) 2 occupying the first post-operative drain compartment 12. The reservoir 2 is connected to a drain (7 mm×20 cm) 3. In another example, there may be a reservoir of a post-operative drain occupying each post-operative drain compartment.

Figure 8:
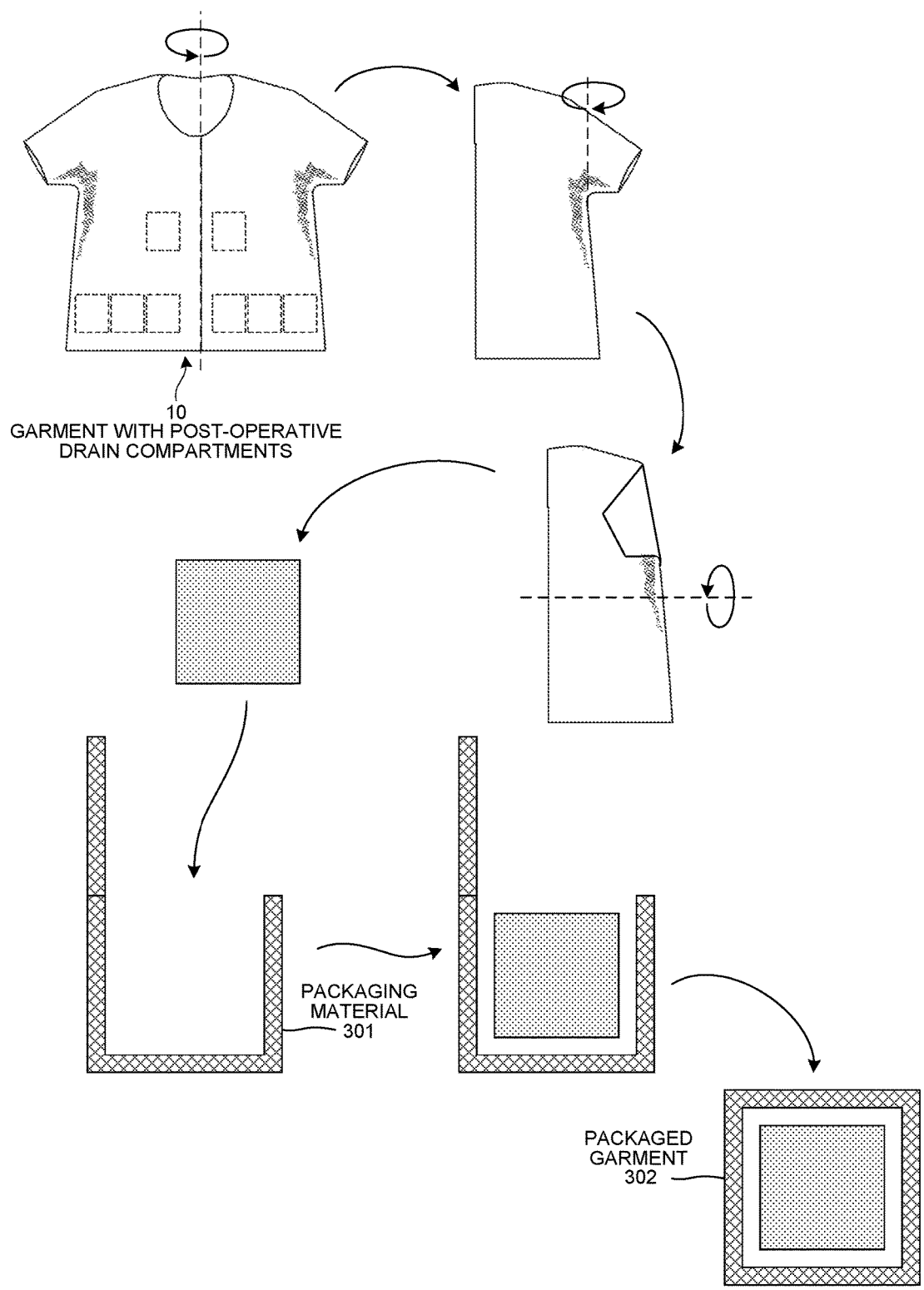
FIG. 8 is a diagram showing how to package a garment having post-operative drain compartments.

In second step (step 102), the garment with post-operative drain compartments is packed using packaging material. In the example in FIG. 8, the garment 10 is folded compactly and packaged into the packaging material 301. The packaged garment 302 is then distributed to medical retailers or other sales distribution channels.

Although certain specific exemplary embodiments are described above in order to illustrate the invention, the invention is not limited to the specific embodiments. For example, although the garment is shown as a t-shirt, in other embodiments, the garment may be a long sleeve shirt, a pajama, a vest, a zip, a coat, and a jacket. The example of FIG. 2 has a set of compartments on each side, however, in other embodiments, the compartments are all disposed along a single side. Although the compartments of FIG. 2 have one compartment above three lower compartments, in another example, the compartments have two upper compartments that are aligned between first and second axes 13,14 and two lower compartments that are aligned between the third and fourth axes 16,17. In yet another example, there are compartments situated vertically between two other compartments. For example, one compartment is disposed above a second compartment, which in turn, is disposed above a third compartment. The first, second and third compartments are stacked vertically. In another embodiment, the compartments are disposed along a grid pattern such that a compartment is selectively disposed at along elements of the grid pattern. The grid has dimensions A×B taken from group consisting of: 1×1, 1×2, 1×3, 1×4, 2×1, 2×2, 2×3, 3×4, 3×1, 3×2, 3×3, 3×4, and 4×1, 4×2, 4×3, and 4×4. The dimension "A" represents the number of compartments horizontally along the grid (for example, parallel to the first axis 13) and the dimension "B" represents the number of compartments vertically along the grid (for example, parallel to the fifth axis 20). One or more of grids may selectively not have any compartment to provide a gap between the compartments. Accordingly, various modifications, adaptations, and combinations of various features of the described embodiments can be practiced without departing from the scope of the invention as set forth in the claims.

What is claimed is:

1. A garment comprising:
   an inner surface;
   an outer surface;
   a front panel comprising a left front panel and a right front panel;
   a rear panel; and
   a plurality of post-operative drain compartments disposed along the inner surface of the garment, wherein a first of the plurality of post-operative drain compartments is disposed between a first axis and a second axis, wherein the first post-operative drain compartment has an upper edge, a lower edge, and two side edges, wherein the upper edge of the first post-operative drain compartment provides a first opening, wherein the first post-operative drain compartment has a length and a width, wherein the two side edges of the first post-operative drain compartment extend parallel to the length, wherein the upper edge and the lower edge of the first post-operative drain compartment extend parallel to the width, wherein the first post-operative drain compartment is disposed above a navel portion of the garment, wherein the first post-operative drain compartment is disposed below a breast portion of the garment, wherein a second of the plurality of post-operative drain compartments is disposed between a third axis and a fourth axis, wherein a third of the plurality of post-operative drain compartments is disposed between the third axis and the fourth axis, wherein the first post-operative drain compartment is also disposed between a fifth axis and a sixth axis, wherein a fourth of the plurality of post-operative drain compartments is disposed between the fifth axis and the sixth axis, and between the third axis and the fourth axis, wherein the fourth post-operative drain compartment has an upper edge and a lower edge, wherein the upper edge of the fourth post-operative drain compartment provides a second opening, wherein a distance between the upper edge of the fourth post-operative drain compartment and the lower edge of the first post-operative drain compartment is greater than half of the length of the first post-operative drain compartment, wherein the upper edge of the fourth post-operative drain compartment and the lower edge of the first post-operative drain compartment define a space which is free of any post-operative drain compartments, wherein the fourth post-operative drain compartment is disposed below the navel portion of the garment, wherein the second post-operative drain compartment is adjacent to the third post-operative drain compartment, wherein the second and third post-operative drain compartments are disposed below the first post-operative drain compartment, wherein the first, second, third, and fourth axes are parallel to each other, wherein the first, second, third, and fourth post-operative drain compartments are all disposed on one of either the left front panel or the right front panel, and wherein the first, second, third, and fourth post-operative drain compartments are all disposed on the inner surface of the garment.

2. The garment of claim 1, wherein each of the post-operative drain compartments has a rectangular shape, and wherein each of the post-operative drain compartments is of a substantially same size.

3. The garment of claim 1, wherein the fifth axis is parallel to the sixth axis, and wherein the fifth axis is perpendicular to the first axis.

4. The garment of claim 3, wherein an edge of the third post-operative drain compartment is adjacent to the fifth axis.

5. The garment of claim 3, wherein the fourth post-operative drain compartment is adjacent to the third post-operative drain compartment.

6. The garment of claim 1, further comprising:
a second plurality of post-operative drain compartments disposed along the inner surface of the garment, wherein the first plurality of post-operative drain compartments is disposed on one of either the left front panel or the right front panel and the second plurality of post-operative drain compartments is disposed on an other of either the left front panel or the right front panel.

7. The garment of claim 6, wherein at least one of the second plurality of post-operative drain compartments is disposed between the first axis and the second axis, and wherein at least one of the second plurality of post-operative drain compartments is disposed between the third axis and fourth axis.

8. The garment of claim 1, wherein the garment has at least four post-operative drain compartments.

9. The garment of claim 1, wherein the second axis is disposed above a navel of a user of the garment.

10. The garment of claim 1, wherein the second, third, and fourth post-operative drain compartments are disposed along a lower edge of the garment.

11. The garment of claim 1, wherein the distance between the upper edge of the fourth post-operative drain compartment and the lower edge of the first post-operative drain compartment is at least three inches.

12. The garment of claim 1, wherein the upper edge of the fourth post-operative drain compartment is parallel to the upper edge of the first post-operative drain compartment, and wherein the lower edge of the fourth post-operative drain compartment is parallel to the upper edge of the first post-operative drain compartment.

13. A method comprising:
forming a plurality of post-operative drain compartments on either a left front panel or a right front panel of a garment, wherein the garment has a front panel and rear panel, wherein the front panel comprises the left front panel and the right front panel, wherein the plurality of post-operative drain compartments includes at least four post-operative drain compartments all of which are formed on either the left front panel or the right front panel of the garment, wherein the at least four post-operative drain compartments are all formed within an interior of the garment, wherein a first of the plurality of post-operative drain compartments is disposed between a first axis and a second axis, wherein the first post-operative drain compartment has an upper edge, a lower edge, and two side edges, wherein the upper edge of the first post-operative drain compartment provides a first opening, wherein the first post-operative drain compartment has a length and a width, wherein the two side edges of the first post-operative drain compartment extend parallel to the length, wherein the upper edge and the lower edge of the first post-operative drain compartment extend parallel to the width, wherein the first post-operative drain compartment is disposed above a navel portion of the garment, wherein the first post-operative drain compartment is disposed below a breast portion of the garment, wherein a second of the plurality of post-operative drain compartments is disposed between a third axis and a fourth axis, wherein a third of the plurality of post-operative drain compartments is disposed between the third axis and the fourth axis, wherein the first post-operative drain compartment is disposed between a fifth axis and a sixth axis, wherein a fourth of the plurality of post-operative drain compartments is disposed between the fifth axis and the sixth axis, and between the third axis and the fourth axis, wherein the fourth post-operative drain compartment has an upper edge and a lower edge, wherein the upper edge of the fourth post-operative drain compartment provides a second opening, wherein a distance between the upper edge of the fourth post-operative drain compartment and the lower edge of the first post-operative drain compartment is greater than half of the length of the first post-operative drain compartment, wherein the upper edge of the fourth post-operative drain compartment and the lower edge of the first post-operative drain compartment define a space which is free of any post-operative drain compartments, wherein the fourth post-operative drain compartment is disposed below the navel portion of the garment, wherein the second post-operative drain compartment is adjacent to the third post-operative drain compartment, wherein the second and third post-operative drain compartments are disposed below the first post-operative drain compartment, wherein the first, second, third, and fourth axes are parallel to each other and, wherein the first, second, third, and fourth post-operative drain compartments are all disposed on one of either the left front panel or the right front panel, and wherein the first, second, third, and fourth post-operative drain compartments are all disposed on the inner surface of the garment.

14. The method of claim 13, wherein each of the post-operative drain compartments has a rectangular shape, and wherein each of the post-operative drain compartments is of a substantially same size.

15. The method of claim 13, wherein the fifth axis is parallel to the sixth axis, and wherein fifth axis is perpendicular to the first axis.

16. The method of claim 15, wherein an edge of the third post-operative drain compartment is adjacent to the fifth axis.

17. The method of claim 15, wherein the fourth post-operative drain compartment is adjacent to the third post-operative drain compartment.

\* \* \* \* \*